US012527568B2

(12) United States Patent
Johnson et al.

(10) Patent No.: US 12,527,568 B2
(45) Date of Patent: Jan. 20, 2026

(54) SUTURING DEVICE WITH REPLACEABLE DISTAL END

(71) Applicant: Durastat LLC, Austin, TX (US)

(72) Inventors: Jens Johnson, Austin, TX (US); Adam Azzara, Austin, TX (US); Kevin T. Foley, Memphis, TN (US); Michael J. Milella, Jr., San Diego, CA (US)

(73) Assignee: DURASTAT LLC, Austin, TX (US)

( * ) Notice: Subject to any disclaimer, the term of this patent is extended or adjusted under 35 U.S.C. 154(b) by 48 days.

(21) Appl. No.: 18/670,964

(22) Filed: May 22, 2024

(65) Prior Publication Data

US 2025/0331845 A1 Oct. 30, 2025

Related U.S. Application Data

(60) Provisional application No. 63/640,574, filed on Apr. 30, 2024.

(51) Int. Cl.

*A61B 17/04* (2006.01)
*A61B 17/00* (2006.01)
*A61B 17/06* (2006.01)

(52) U.S. Cl.

CPC .................... *A61B 17/0469* (2013.01); *A61B 2017/00367* (2013.01); *A61B 2017/00862* (2013.01); *A61B 2017/0608* (2013.01)

(58) Field of Classification Search

CPC ................................................. A61B 17/0469
See application file for complete search history.

(56) References Cited

U.S. PATENT DOCUMENTS

| | | | | |
|---|---|---|---|---|
| 10,918,379 | B2 * | 2/2021 | Kurd | A61B 17/06109 |
| 2019/0021723 | A1 * | 1/2019 | Anderson | A61B 17/2841 |
| 2022/0218330 | A1 * | 7/2022 | Oka | A61B 17/062 |

* cited by examiner

*Primary Examiner* — Todd J Scherbel
(74) *Attorney, Agent, or Firm* — RANKIN, HILL & CLARK LLP

(57) ABSTRACT

A suturing device includes a cannula, a distal end assembly removably connected to the cannula, a needle pusher provided in the cannula and extending into the distal end assembly when the distal end assembly is connected with the cannula, a primer movable between an extended position and a depressed position, and a spring positioned between the primer and the needle pusher. The distal end assembly includes a needle compartment defining a needle passage terminating in a distal opening. Movement of the primer from the extended position toward the depressed position compresses the spring to exert a biasing force on the needle pusher in an advance direction when the primer is in the depressed position. The primer is operatively connected with the needle pusher such that movement of the primer from the depressed position toward the extended position moves the needle pusher in a retract direction.

18 Claims, 10 Drawing Sheets

SUTURING DEVICE WITH REPLACEABLE DISTAL END

BACKGROUND

The present disclosure relates generally to surgery and the placement of sutures, and more particularly to devices and methods for suture repair of the tissue.

Surgical closure using sutures is one approach to tissue repair. Oftentimes a needle driver or similar device is used to locate and to pass a suture needle through the tissue to be repaired. The suture needle attaches at one end to a predetermined length of suture, which can be stored in a suture package. Other wound closure devices, such as staples, and other repair devices, like mesh or patch reinforcements, are frequently used for repair.

Locating the tissue repair devices, especially when working in areas where it is difficult for a surgeon to access such as when working through a tubular retractor or other portal, can be very challenging. U.S. Pat. No. 10,610,215 B2 discloses a suturing device that includes an elongate body, a needle holder, and an actuator. The needle holder defines a needle passage that holds a needle. The actuator is configured such that movement from a first operating position toward a second operating position moves the needle in an advance direction. The actuator includes a button and a spring biasing the actuator toward the second operating position. The button is operatively connected with the spring so as to preclude the spring from moving the actuator toward the second operating position until after the button has been moved from a non-actuated position toward an actuated position. The suturing device disclosed in U.S. Pat. No. 10,610,215 B2 is particularly well suited for delivering one needle; however, reloading the device with another needle or the same needle that had been deployed can be problematic.

SUMMARY

In view of the foregoing, a suturing device includes a cannula, a distal end assembly removably connected to the cannula, a needle pusher provided in the cannula and extending into the distal end assembly when the distal end assembly is connected with the cannula, a primer movable between an extended position and a depressed position, and a spring positioned between the primer and the needle pusher. The distal end assembly includes a needle compartment defining a needle passage terminating in a distal opening. Movement of the primer from the extended position toward the depressed position compresses the spring to exert a biasing force on the needle pusher in an advance direction when the primer is in the depressed position. The primer is operatively connected with the needle pusher such that movement of the primer from the depressed position toward the extended position moves the needle pusher in a retract direction, which is opposite the advance direction.

DETAILED DESCRIPTION

Figure 1:
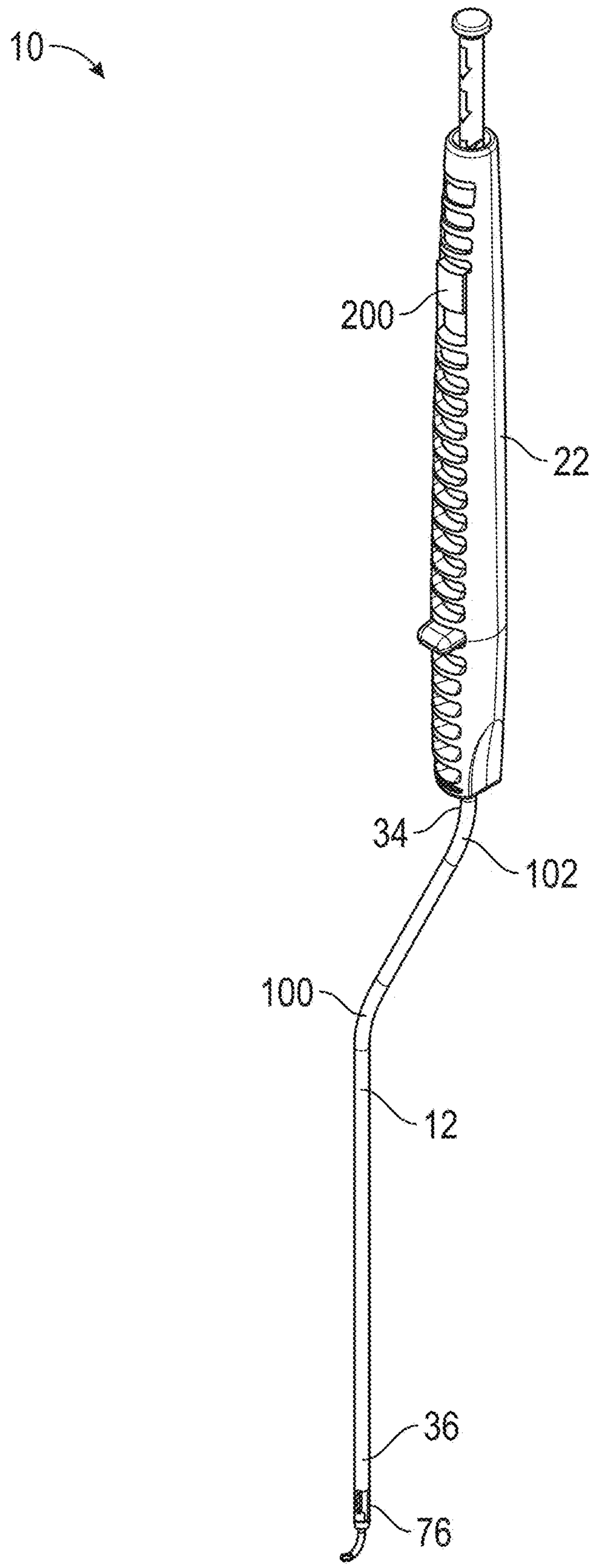
FIG. 1 is a perspective view of a suturing device.
Figure 2:
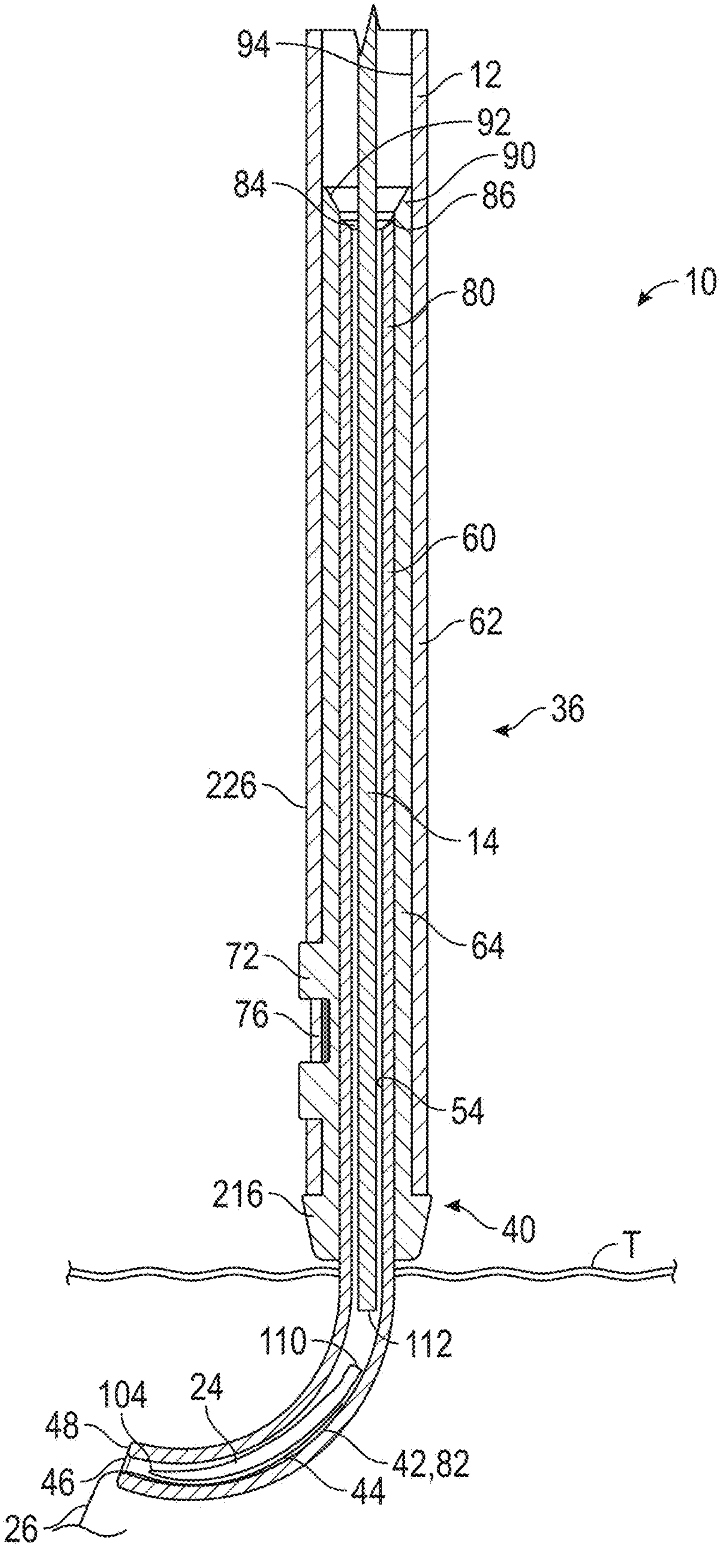
FIG. 2 is a cross-sectional view of the lower portion of the suturing device depicted in FIG. 1 positioned to repair a tissue tear or incision.
Figure 3:
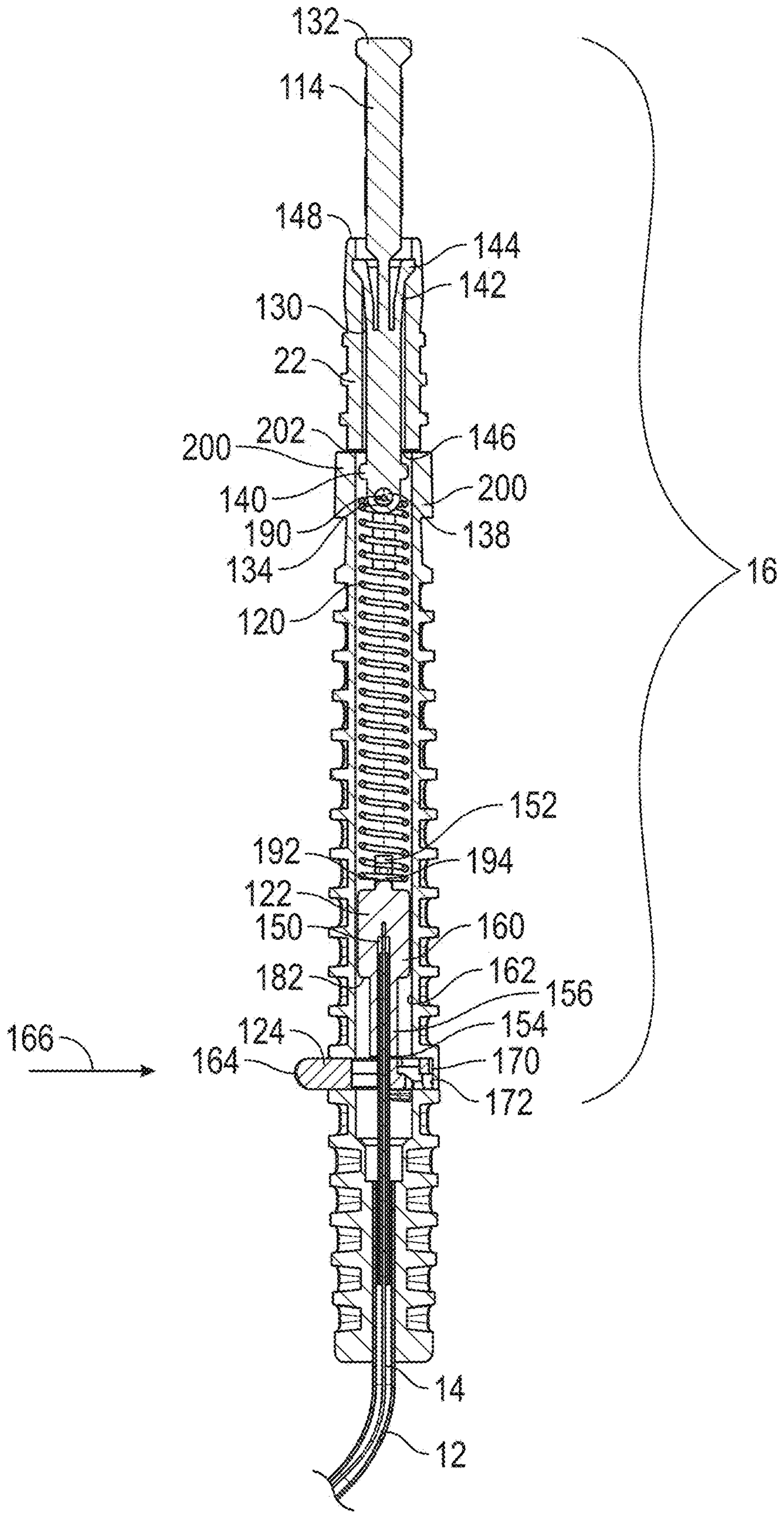
FIG. 3 is a cross-sectional view of a proximal portion of the suturing device depicted in FIG. 1 with a primer in an extended position.
Figure 4:
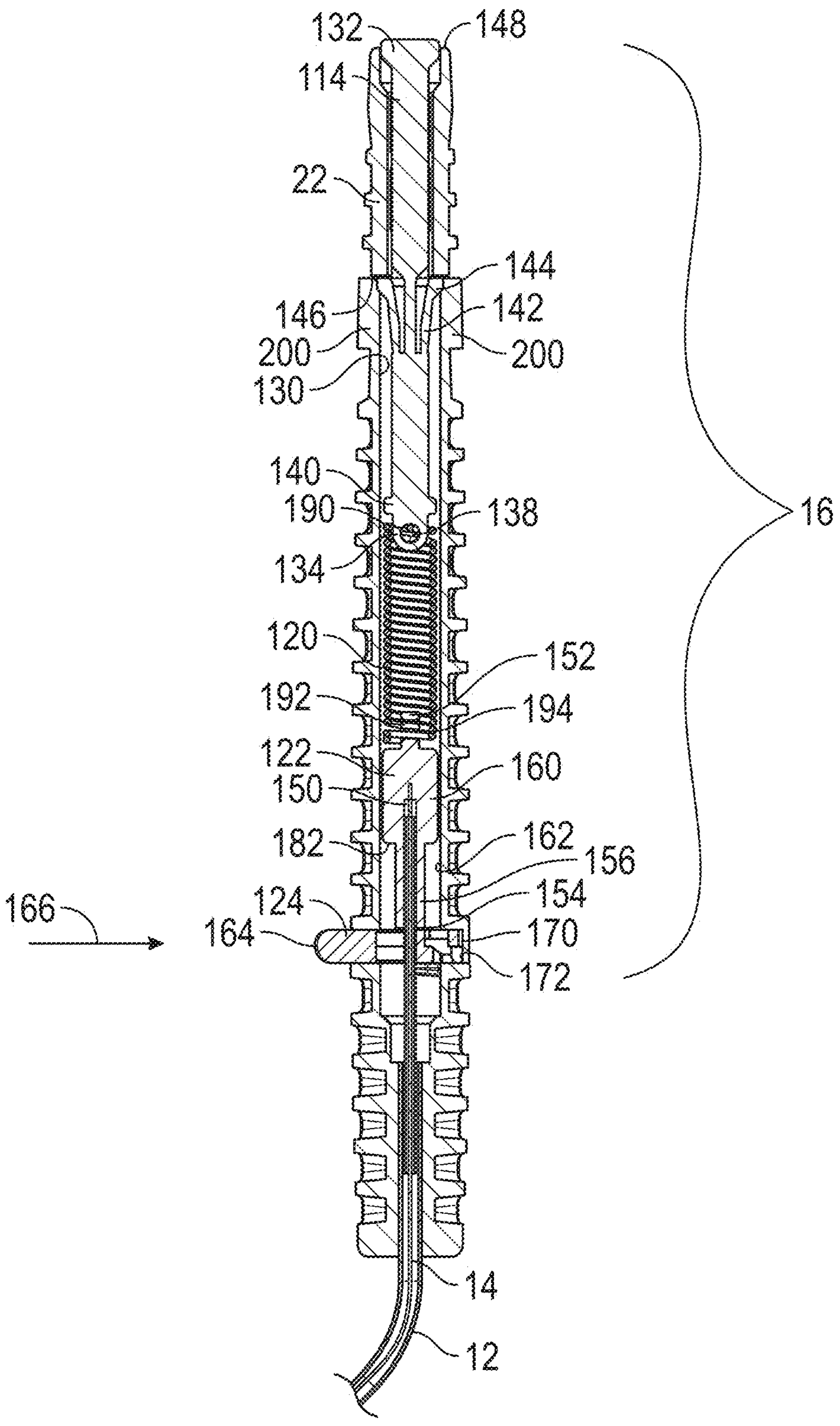
FIG. 4 is a cross-sectional view of a proximal portion of the suturing device depicted in FIG. 1 with a primer in a depressed position.

FIGS. 1-4 depict a suturing device 10 including a cannula 12 (FIG. 1), a needle pusher 14 (FIGS. 2, 3 and 4) and an actuator mechanism 16 (FIGS. 3 and 4). With reference to FIG. 1, the suturing device 10 can further include a handle 22 connected with the cannula 12. With reference to FIG. 2, the suturing device 10 can further include a needle 24 and a suture 26 connected with the needle 24. While, as depicted, the needle 24 is curved, the needle 24 can take different configurations, e.g., straight, without departing from the scope of the present application. The suturing device 10 is useful to repair tissue tears. The suturing device 10 can be particularly useful during a minimally invasive surgical procedure that is performed through a tubular retractor or other small surgical portal to accurately locate the needle 24 and the suture 26 to facilitate passing the needle 24 through target tissue T to be sutured; however the suturing device 10 is useful in other suturing procedures.

With reference to FIG. 1, the cannula 12 includes a proximal portion 34 and a distal portion 36. The proximal portion 34 is located nearer to and/or can be partially received in the handle 22. As seen in FIG. 2, the distal portion 36 receives a distal end assembly 40 that includes a needle compartment 42 that defines a needle passage 44 terminating in a distal opening 46. A distal edge surface 48 of the needle compartment 42 defines the distal opening 46. More particular to the embodiment disclosed in FIG. 2, the needle compartment 42 defines the needle passage 44, which is curved and extends along a curved needle passage axis. This aids in accommodating the needle 24, which can also be curved, in the needle passage 44. As illustrated, the needle compartment 42 has an arc length less 180 degrees, although the arc length could be longer.

As illustrated in FIG. 2, the distal end assembly 40 includes a tube 60 received in an insert 64. As depicted, the tube 60 is held in the distal portion 36 of the cannula 12 by the insert 64. The tube 60 and the insert 64 together form the distal end assembly 40, which is removably connected with the distal portion 36 of the cannula 12. In this regard, the insert 64 includes a protrusion 72 receivable in a slot 76, which is upside down L-shape as shown in FIG. 1, provided at the distal portion 36 of the cannula 12. The protrusion 72 and the slot 76 are complementary with each other for releasably locking the protrusion 72 in the slot 76, thereby releasably locking the insert 64 with the distal portion 36 of the cannula 12. In the depicted embodiment, the insert 64 and the protrusion 72 are formed from an elastic material, e.g., plastic, to allow the protrusion 72 to deform against the cannula 12, which can be made from stainless steel, when the insert 64 is inserted into the slot 76 the distal portion 36 of the cannula 12 and then rotated. The tube 60 can be formed from stainless steel, and the insert 64 can be over-molded onto the tube 60.

The distal end assembly 40 is removable from the distal portion 36 of the cannula 12 such that when the needle 24 and the suture 26 have been ejected from the needle passage 44, the distal end assembly 40 may be removed from the distal portion 36 of the cannula 12 and replaced with a similar distal end assembly having a needle and suture stored in a needle passage, for passing another suture through the target tissue T with the suturing device 10.

With reference to FIG. 2, the tube 60 includes a proximal section 80 disposed in and at least partially surrounded by the insert 64 and a distal section 82 that forms the needle compartment 42 defining the needle passage 44 terminating in the distal opening 46. The distal section 82 extends from the proximal section 80 and the insert 64, which allows the distal section 82 to have a smaller outer diameter as compared to the outer diameter of the distal portion 36 of the cannula 12. The proximal section 80 of the tube 60 includes a proximal chamfered surface 84 inclined from an internal surface 86 of the insert 64 toward an interior of the tube 60. The proximal chamfered surface 84 guides the needle pusher 14 into the tube 60 when the distal end assembly 40 is being connected with the cannula 12.

The insert 64 includes insert includes a proximal end 90 disposed in the cannula 12 and a proximal angled surface 92 inclined from an inner surface 94 of the cannula 12 toward an interior of the insert 64. The proximal angled surface 92 guides the needle pusher 14 into the insert 64 when the distal end assembly 40 is being connected with the distal portion 36 of the cannula 12. As depicted, the proximal chamfered surface 84 is substantially aligned with the proximal angled surface 92 to form a continuous inclined surface that guides the needle pusher 14 into the insert 64 and the tube 60 when the distal end assembly 40 is inserted into the distal portion 36 of the cannula 12.

In the depicted embodiments, the cannula 12 is circular in a cross section taken normal to the longest dimension of the cannula 12, however, the cannula 12 could take alternative configurations, such as polygonal or U-shaped. The cannula 12 has a bayonet configuration in the illustrated embodiment; however, the cannula 12 could take alternative configurations, such as straight along a longitudinal axis. As illustrated in FIG. 1, the cannula 12 includes a more distal bend 100 and a more proximal bend 102 to form the bayonet configuration.

With reference to FIGS. 3 and 4, the needle pusher 14 is operably connected with the actuator mechanism 16. The needle pusher 14 can be a wire, which can be made from nitinol. The needle pusher 14 is received in the cannula 12. More particularly, the needle pusher 14 is received in a needle pusher passage 54 located within the cannula 12 that extends into the distal end assembly 40. Upon actuation of the actuator mechanism 16, which will be described in more detail below, the needle pusher 14 is configured to push the needle 24 in an advance direction through the distal opening 46. With reference to FIG. 2, the needle 24 includes a first end 104, which is pointed, and a second end 110 that is opposite the first end 104. The suture 26 connects with the second end 110 of the needle 24. In the illustrated embodiment, at least a portion of the suture 26 extends through the distal opening 46 when the needle 24 is received in the needle compartment 42 prior to the actuator mechanism 16 being actuated.

Prior to actuation of the actuator mechanism 16, a distal end 112 of the needle pusher 14 is offset from the second end 110 of the needle 24. Although not shown in FIG. 2, prior to actuation of the actuator mechanism 16 a portion of the needle pusher 14 may extend into the needle passage 44. The needle pusher passage 54 also extends through the more distal bend 100 and the more proximal bend 102 in the cannula 12, depicted in FIG. 1, located in the proximal portion 34 of the cannula 12.

With reference to FIGS. 3 and 4, the actuator mechanism 16 is operably connected with the needle pusher 14. The actuator mechanism 16 includes a primer 114, a spring 120, a shuttle 122, and a button 124. The primer 114 is movable between an extended position shown in FIG. 3 and a depressed position shown in FIG. 4. The spring 120 is positioned between and connected with the primer 114 and the shuttle 122. When the button 124 is not depressed, movement of the primer 114 from the extended position toward the depressed position compresses the spring 120 against the shuttle 122. The spring 120 exerts a biasing force on the shuttle 122 in the advance direction when the primer 114 is in the depressed position. The button 124 is operably engaged with the shuttle 122. The spring 120 biases the shuttle 122 in the advance direction after the button 124 is depressed, which moves the needle pusher 14 and pushes the needle 24 in the advance direction through the distal opening 46.

The primer 114 is received in an upper bore 130 provided in the handle 22. The primer 114 includes a proximal head 132 and a distal end portion 134. A primer eyelet 138 is provided in the distal end portion 134 and a radial shoulder 140 is offset from the primer eyelet 138 toward the proximal head 132. The distal end portion 134, the primer eyelet 138 and the radial shoulder 140 operate as a locating feature for the spring 120, which will be described in more detail below.

The primer 114 further includes a resilient finger 142 (two resilient fingers are shown in FIGS. 3 and 4). A barb 144 is provided at a distal end of each resilient finger 142. As mentioned above, the primer 114 is movable between the extended position shown in FIG. 3, and the depressed position shown in FIG. 4 where the proximal head 132 is brought closer to and can come in contact with a proximal end 148 of the handle 22. A thumb of the operator of the suturing device 10 can be used to depress the primer 114, moving the primer 114 from the extended position toward the depressed position. A shoulder 146 can be provided in the handle 22 and the radial shoulder 140 can contact the shoulder 146 in the handle 22 when the primer 114 is in the extended position. As the primer 114 is depressed, the resilient fingers 142 compress while traveling through the upper bore 130 until passing the shoulder 146 in the handle 22 in the depressed position. When in the depressed position, the resilient finger 142, and more particularly the barb 144 on the resilient finger 142, selectively engages the shoulder 146 in the handle 22 to maintain the primer 114 in the depressed position.

The shuttle 122 includes a bore 150, which receives the needle pusher 14 to connect the needle pusher 14 with the shuttle 122. The needle pusher 14 is fixed to the shuttle 122 such that movement of the shuttle 122 results in movement of the needle pusher 14. The shuttle 122 includes a proximal end portion 152 that provides a locating feature for the spring 120. The shuttle 122 also includes a button contact surface 154, which is a distal end surface of the shuttle 122 as illustrated in FIGS. 3 and 4. The shuttle 122 also includes a reduced cross-sectional portion 156 extending from a relatively larger cross-sectional portion 160. The relatively larger cross-sectional portion 160 has a diameter slightly smaller than an inner diameter of an actuator cavity 162 provided in the handle to allow for translational movement of the shuttle 122 within the actuator cavity 162.

The button 124 includes an operator contact surface 164 and operates as a push button in the illustrated embodiment whereby an operator, such as a surgeon, depresses the button 124 in the direction of arrow 166 moving the button 124 from the non-actuated position toward the actuated position. The button 124 also includes a finger 170 (see also FIG. 5) which contacts an inner side surface 172 provided in the handle 22 to bias the button 124 toward the non-actuated position. As the operator depresses the button 124 in the direction of arrow 166, the finger 170 bends and operates similar to a spring.

Figure 5:
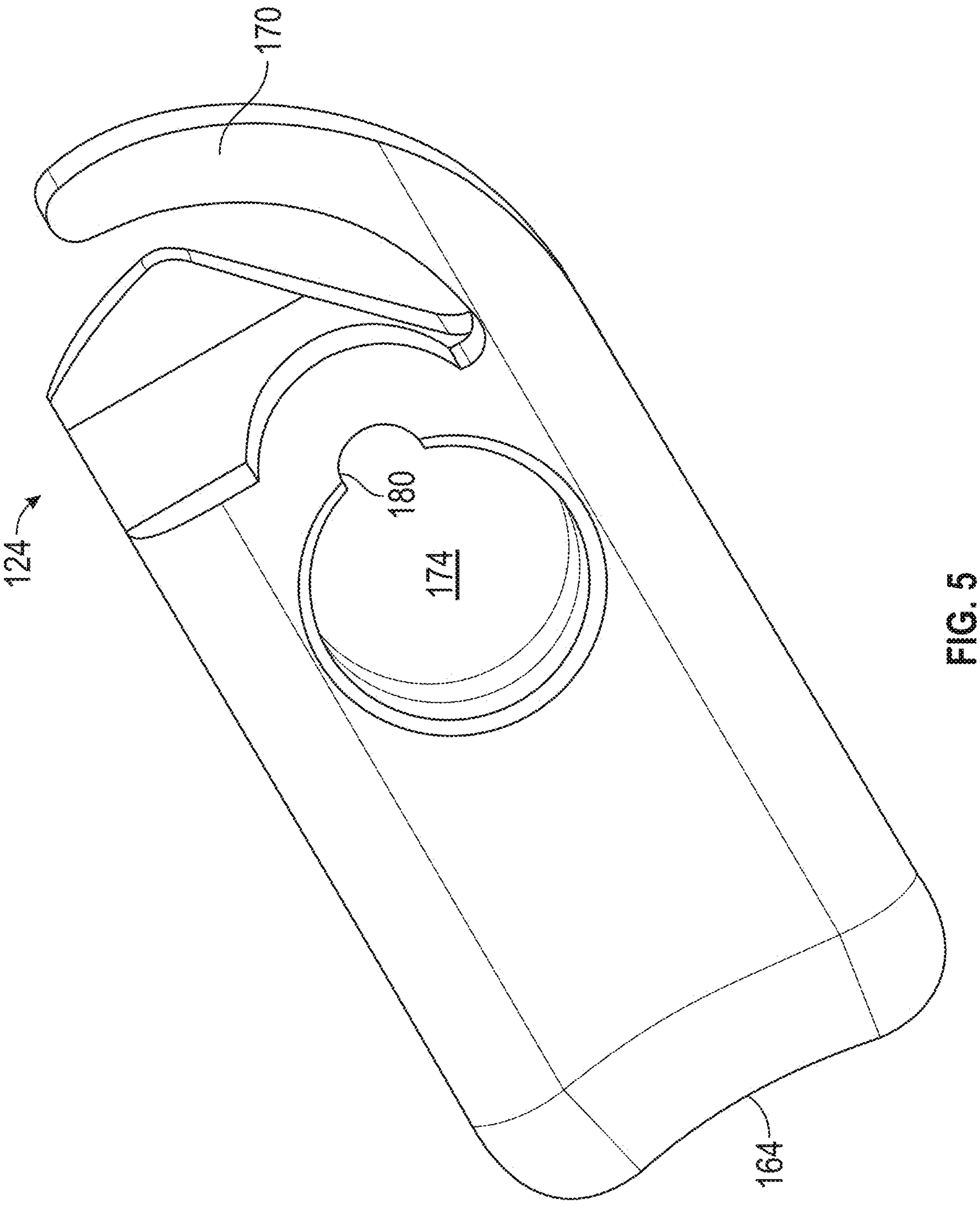
FIG. 5 is a perspective view of a button of the suturing device of FIG. 1

As more clearly seen in FIG. 5, the button 124 includes an opening made up of a main portion 174 and a smaller portion 180. The main portion 174 of the opening is configured to receive the reduced cross-sectional portion 156 of the shuttle 122 when the main portion 174 of the opening is aligned with the reduced cross-sectional portion 156. This occurs when the operator presses the operator contact surface 164 in the direction of arrow 166 thus moving the button 124 to the right per the orientation shown in FIG. 3. The main portion 174 of the opening, however, is smaller than the relatively larger cross-sectional portion 160 of the shuttle 122. Accordingly, the travel distance of the shuttle 122 is limited by the distance between the button contact surface 154 and a transition surface 182 where the reduced cross-sectional portion 156 transitions to the relatively larger cross-sectional portion 160. With reference back to FIG. 5, the smaller portion 180 of the slider opening is configured to allow for passage of the needle pusher 14 to allow for the connection of the needle pusher 14 to the shuttle 122. When the button 124 is in the non-actuated position (shown in FIGS. 1, 3 and 4), the button 124 contacts the shuttle 122 to preclude movement of the shuttle 122 with respect to the button 124. When an operator moves the button 124 in the direction of arrow 166, the button 124 is moved in the direction of arrow 166 which allows the main portion 174 of the slider opening to align with the reduced cross-sectional portion 156 of the shuttle 122, and the spring 120 moves the shuttle 122 downwardly (per the orientation shown in FIG. 4) such that the reduced cross-sectional portion 156 passes through the main portion 174 of the opening thus moving the needle pusher 14 and thus moving the needle 24 in the advance direction toward the distal opening 46.

In the embodiment depicted in FIGS. 3 and 4, the spring 120 is interposed between and connects the primer 114 with the shuttle 122. The primer 114 defines the primer eyelet 138, and the spring 120 includes a first end portion 190 which extends through the primer eyelet 138 such that the primer 114 is fixed with the first end portion 190. The shuttle 122 defines a shuttle eyelet 192. The spring 120 includes a second end portion 194 which extends through the shuttle eyelet 192 such that the shuttle 122 is fixed with the shuttle 122. In this manner, the spring 120 is fixed with each of the primer 114 and the shuttle 122 for exerting biasing forces on the shuttle 122 based on a position of the primer 114. The spring 120 is useful to pull the primer 114, and more particularly the reduced cross-sectional portion 156, back through the main portion 174 of the slider opening after the needle 24 has been deployed. This is useful when replacing the distal end assembly 40 with a similar distal end assembly having a needle and suture stored in a needle passage, for passing another suture through the target tissue T with the suturing device 10.

When the primer 114 is in the depressed position, the spring 120 elastically compresses between the primer 114 and the shuttle 122 and exerts a force on the shuttle 122 capable of moving the shuttle 122 and the needle pusher 14 in the advance direction. Because of the manner the spring 120 connects with the primer 114 and the shuttle 122, movement of the primer 114 from the depressed position toward the extended position results in movement of the shuttle 122 and the needle pusher 14 in the retract direction. Because the finger 170 operates similar to a spring, the button 124 returns to a non-actuated position when the primer 114 is from the depressed position to the extended position.

The primer 114 can be operatively connected with the needle pusher 14 in other manners such that movement of the primer 114 from the depressed position toward the extended position moves the needle pusher 14 in a retract direction, which is opposite the advance direction. For example, a tether, which is described in more detail in U.S. application Ser. No. 18/150,875, which is incorporated by reference, can connect the primer 114 with the shuttle 122.

The handle 22 connects with the cannula 12. The spring 120 and the shuttle 122 are positioned inside the handle 22. The primer 114 and the button 124 are at least partially received in the handle 22, where the button 124 is operably engaged with the shuttle 122, and the primer 114 is operatively engaged with the spring 120. As mentioned above, the primer 114 includes the resilient finger 142, and a portion of the resilient finger 142 selectively engages the shoulder 146 in the handle 22 to maintain the primer 114 in the depressed position as shown in FIG. 4. The handle 22 includes a release button 200 (two release buttons are shown in FIG. 4) aligned with the barb 144 when the barb 144 is engaged with the shoulder 146 when the primer 114 is in the depressed position. A cut out 202 is provided through the handle 22 from an exterior surface into the upper bore 130 to define an upper edge of each release button 200 in the illustrated embodiment, which allows each release button 200 to deflect inwardly. When the release button 200 is pressed by a user, the release button 200 is configured to deform inwards toward the barb 144 in the handle 22 to push the barb 144 away from contacting the shoulder 146 to allow the primer 114 to be pulled outwardly from the handle 22 toward the extended position from the depressed position. With the spring 120 connecting the primer 114 with the shuttle 122, movement of the primer 114 from the depressed position toward the extended position pulls the primer 114, and more particularly the reduced cross-sectional portion 156, back through the main portion 174 of the slider opening, which pulls the needle pusher 14 away from the distal opening 46. After the reduced cross-sectional portion 156 is pulled back through the main portion 174 of the slider opening, the finger 170 on the button 124 biases the button in a direction opposite to the arrow 166, which results in the button contact surface 154 on the shuttle 122 contacting the button 124 and the button 124 returning to an undepressed position, which is shown in FIGS. 3 and 4.

Figure 6:
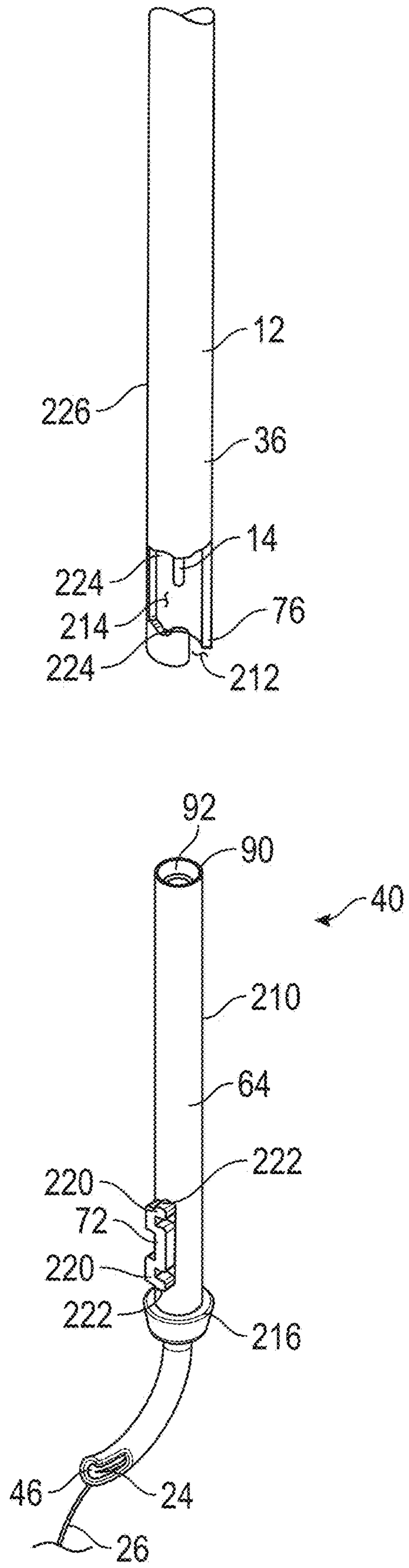
FIG. 6 is a perspective view of a lower portion of the suturing device with a distal end assembly removed.

As seen in FIG. 2, the needle pusher 14 extends into the distal end assembly 40 from the cannula 12 when the distal end assembly 40 is connected with the cannula 12. With reference to FIG. 6, the insert 64 includes an outer surface 210 that mates with the inner surface 94 of the cannula 12 in a sliding, snug fit relationship. The insert 64 can be tubular and the outer surface 210 can be cylindrical, as shown in FIG. 6, which can allow for rotation of the insert 64 within the cannula 12 when the distal end assembly 40 is inserted into the cannula 12.

With continued reference to FIG. 6, the slot 76 includes a first arm 212 extending in a direction in which the insert 64 is inserted in the cannula 12 and a second arm 214 extending from the first arm 212 in a direction perpendicular to the first arm 212. The second arm 214 is configured to receive the protrusion 72 to lock the insert with the cannula 12, which in the illustrated embodiment is in the form of a bayonet connection. The insert 64 includes a shoulder 216 (see also FIG. 2) that abuts the cannula 12 when the insert 64 is inserted into the cannula 12 a distance that positions the protrusion 72 at a junction between the first arm 212 and the second arm 214. The protrusion 72 includes an elastic finger 220 and a tab 222 extended from the elastic finger 220. In the embodiment depicted in FIG. 6, the protrusion 72 includes two elastic fingers 220 (an upper finger and a lower finger per the orientation shown in FIG. 6) and a respective tab 222 on each elastic finger 220. In the second arm 214, a notch 224 extends from the second arm 214 parallel to the direction in which the insert 64 is inserted in the cannula 12. In the embodiment depicted in FIG. 6, two notches 224 are provided; however, only one notch 224 and one elastic finger 220 and one respective tab 222 may be provided. The elastic finger 220 deforms inward against the cannula 12 when the protrusion 72 moves from the first arm 212 into the second arm 214 and expands outward when the tab 222 aligns with the notch 224. With the tab 222 received in the notch 224, translational and rotational movement of the insert 64 with respect to the cannula 12 is inhibited. With reference to FIG. 2, the protrusion 72, and more particularly the elastic finger 220, extends outwardly beyond an external surface 226 of the cannula 12 to allow the elastic finger 220 to be gripped to deflect the elastic finger 220 so that the tab 222 is no longer received in the notch 224 to facilitate rotation of the insert 64 with respect to the cannula 12 during removal of the distal end assembly 40.

Figure 7:
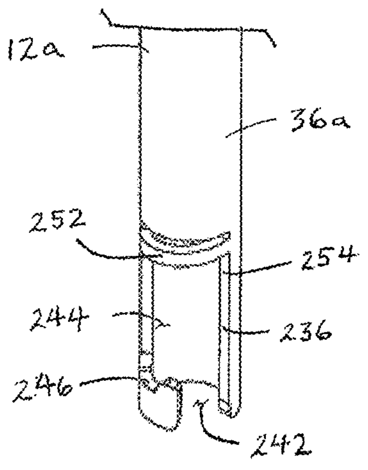
FIG. 7 is a perspective view of a lower portion of an alternative cannula for the suturing device with the distal end assembly removed.
Figure 7:
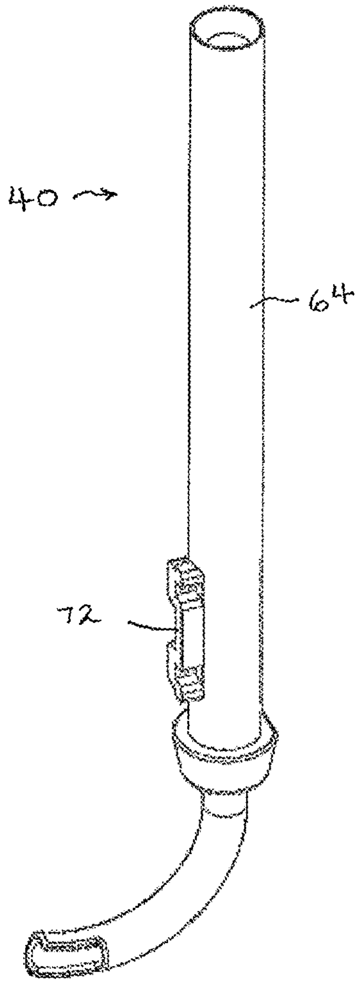
Figure 8:
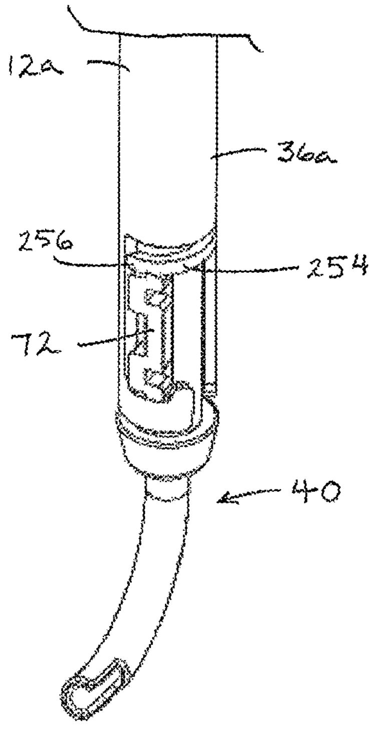
FIG. 8 is a perspective view of the lower portion of the alternative cannula shown in FIG. 7 with the distal end assembly inserted into the alternative cannula.

FIGS. 7 and 8 depict a distal portion **36*a* of a cannula 12*a* for a suturing device that can be similar to the suturing device 10 described above in all respects with the exception of a slot 236, which can operate similarly to the slot 76, which has been described above. The distal end assembly 40 described above fits into the slot 236 in a similar manner to the slot 76 described above. With reference to FIG. 7, the slot 276 includes a first arm 242 extending in a direction in which the insert 64 is inserted in the cannula 12*a* and second arm 244 extending from the first arm 242 in a direction perpendicular to the first arm 242. The second arm 244 is configured to receive the protrusion 72 to lock the insert with the cannula 12*a*, which in the illustrated embodiment is in the form of a bayonet connection. In the second arm 244, a notch 246 extends from the second arm 244 parallel to the direction in which the insert 64 is inserted in the cannula 12*a*. In the embodiment depicted in FIGS. 7 and 8, only a lower notch 246** is provided.

The cannula **12*a* includes a prong 252 extending into the slot 236 that biases the protrusion 72 toward the notch 246 when the protrusion 72 is received in the second arm 244 of the slot 236. The prong 252 extends into the slot 236 from an edge 254 of the slot 236 opposite the second arm 244 and a free end 256 of the prong 252 extends into the second arm 244 of the slot 236. In the illustrated embodiment, the prong 252 is formed by cutting away a portion of the cannula 12*a* at an upper edge of the slot 236 to form the prong 252. Because the cannula 12*a* is formed from stainless steel, the prong 252 can operate as a spring biasing the protrusion 72 toward the notch 246 when the protrusion 72 is received in the second arm 244 of the slot 236**.

Figure 9:
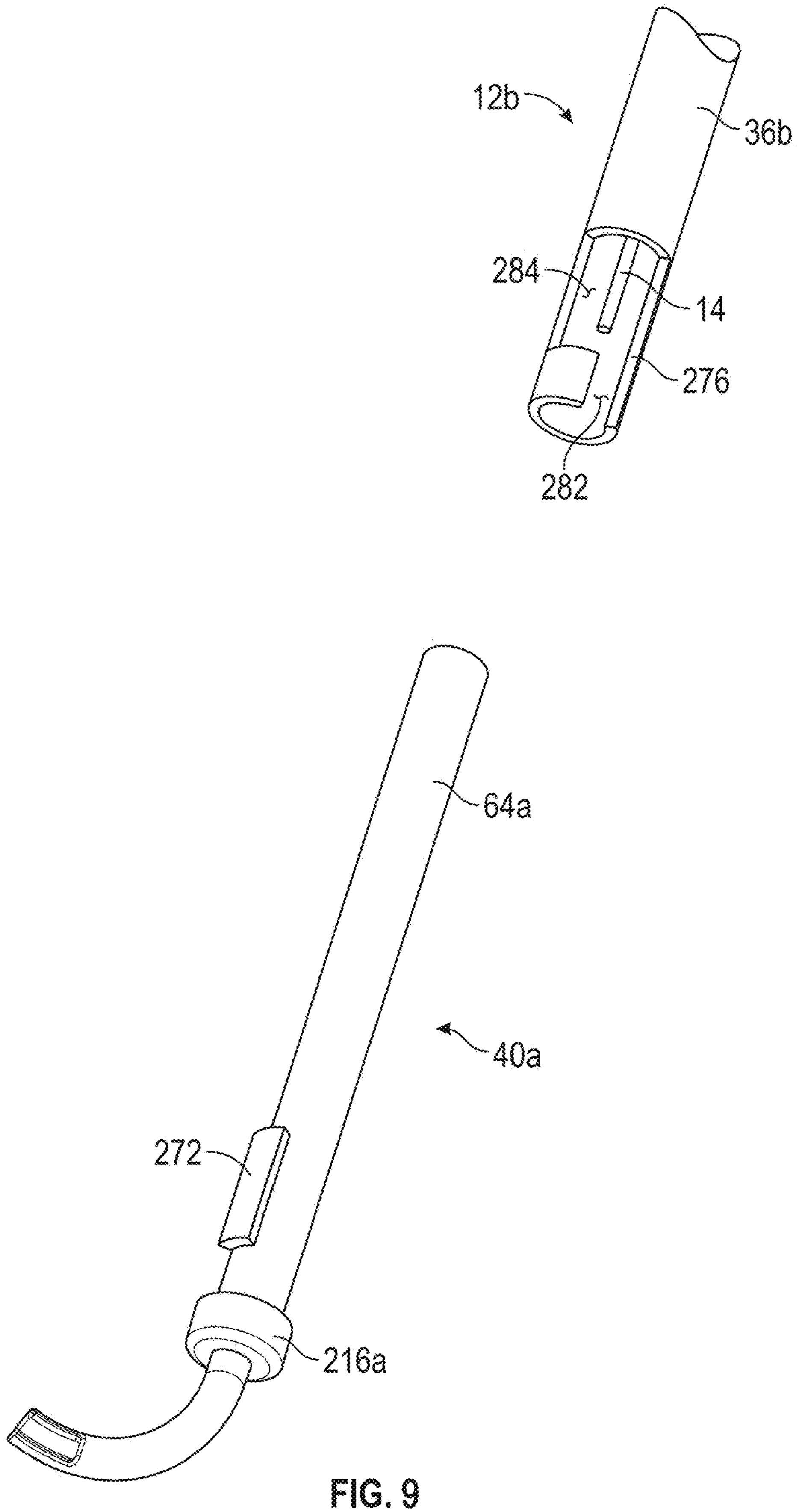
FIG. 9 is a perspective view of a lower portion of another alternative cannula for the suturing device with an alternative distal end assembly removed.
Figure 10:
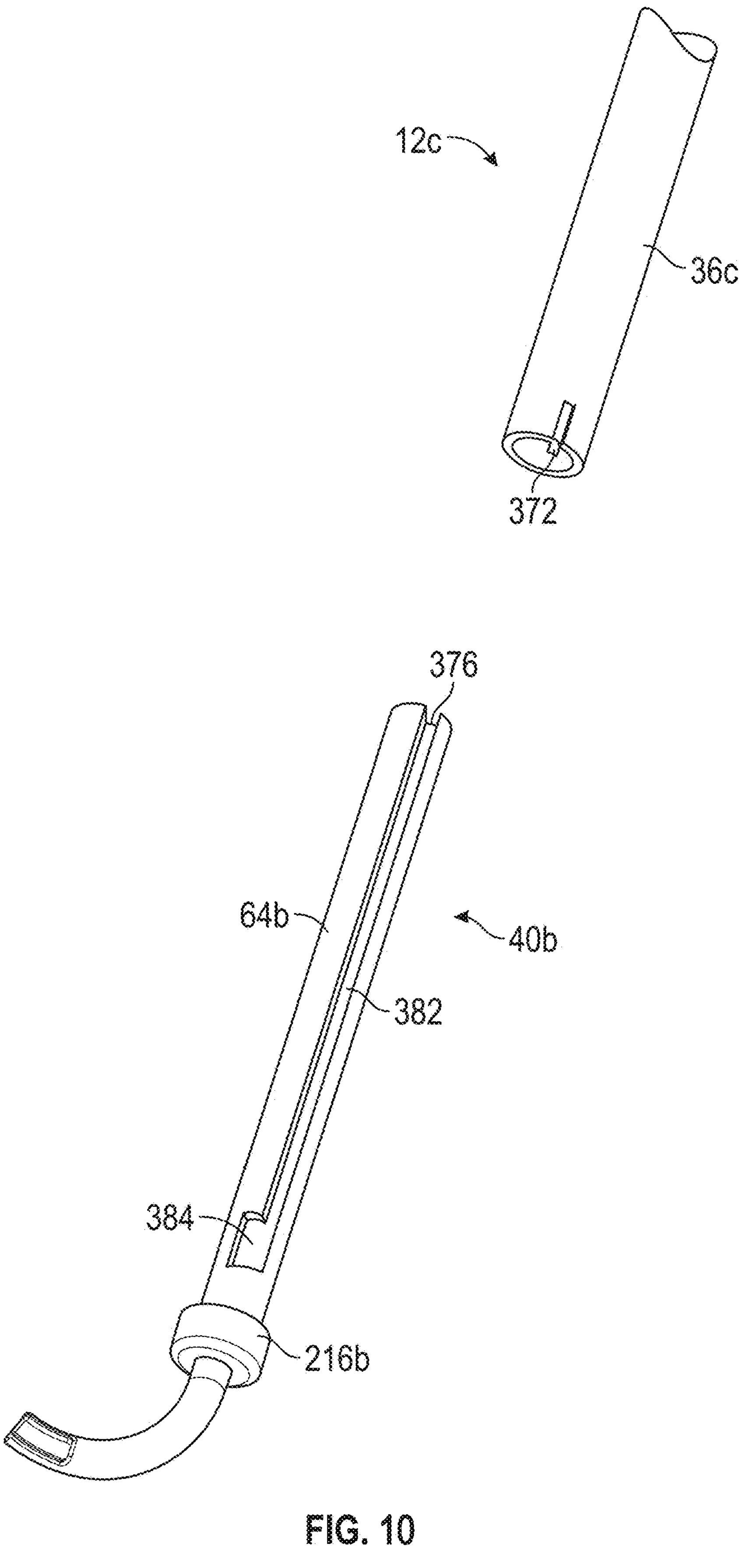
FIG. 10 is a perspective view of a lower portion of yet another alternative cannula for the suturing device with yet another alternative distal end assembly removed.

FIGS. 9 and 10 depict alternative distal end assemblies and alternative distal portions of a suturing device. FIG. 9 depicts a distal portion **36*b* of a cannula 12*b* for a suturing device that can be similar to the suturing device 10 described above in all respects with the exception of a slot 276, which can operate similarly to the slot 76, which has been described above. FIG. 9 also depicts a distal end assembly 40*a* that can be similar to the distal end assembly 40 described above in all respects with the exception of a protrusion 272, which can operate similarly to the protrusion 72**, which has been described above.

The slot 276 includes a first arm 282 extending in a direction in which the insert **64*a* is inserted in the cannula 12*b* and a second arm 284 extending from the first arm 282 in a direction perpendicular to the first arm 282. The second arm 284 is configured to receive the protrusion 272 to lock the insert 64*a* with the cannula 12*b*, which in the illustrated embodiment is in the form of a bayonet connection. The insert 64*a* includes a shoulder 216*a* (similar to shoulder 216 in FIG. 2) that abuts the cannula 12*b* when the insert 64*a* is inserted into the cannula 12*b* a distance that positions the protrusion 272 at a junction between the first arm 282 and the second arm 284. The distal end assembly 40*a* receives the needle pusher 14 in a manner similar to that shown in FIG. 2**.

FIG. 10 depicts a distal portion **36*c* of a cannula 12*c* for a suturing device that can be similar to the suturing device 10 described above in all respects with the exception of a protrusion 372 extends inwardly into an interior of the cannula 12*c*. FIG. 10 also depicts a distal end assembly 40*b* that can be similar to the distal end assembly 40 described above in all respects with the exception of a slot 376 is provided on an insert 64*b* instead of the protrusion 72 described above. Accordingly, one of the cannula 12, 12*a*, 12*b*, 12*c* and the insert 64, 64*a*, 64*b* defines a slot 76, 236, 276, 376 and the other of the cannula 12, 12*a*, 12*b*, 12*c* and the insert 64, 64*a*, 64*b* includes a protrusion 72, 272, 372 receivable in the slot 76, 236, 276, 376 for locking the cannula 12, 12*a*, 12*b*, 12*c* with the insert 64, 64*a*, 64*b*.**

With reference back to FIG. 10, the slot 376 includes a first arm 382 extending in a direction in which the insert **64*b* is inserted in the cannula 12*c* and a second arm 384 extending from the first arm 382 in a direction perpendicular to the first arm 382. The second arm 384 is configured to receive the protrusion 372 to lock the insert 64*b* with the cannula 12*c*, which in the illustrated embodiment is in the form of a bayonet connection. The insert 64*b* includes a shoulder 216*b* (similar to shoulder 216 in FIG. 2) that abuts the cannula 12*c* when the insert 64*b* is inserted into the cannula 12*c* a distance that positions the protrusion 372 at a junction between the first arm 382 and the second arm 384**.

Figure 11:
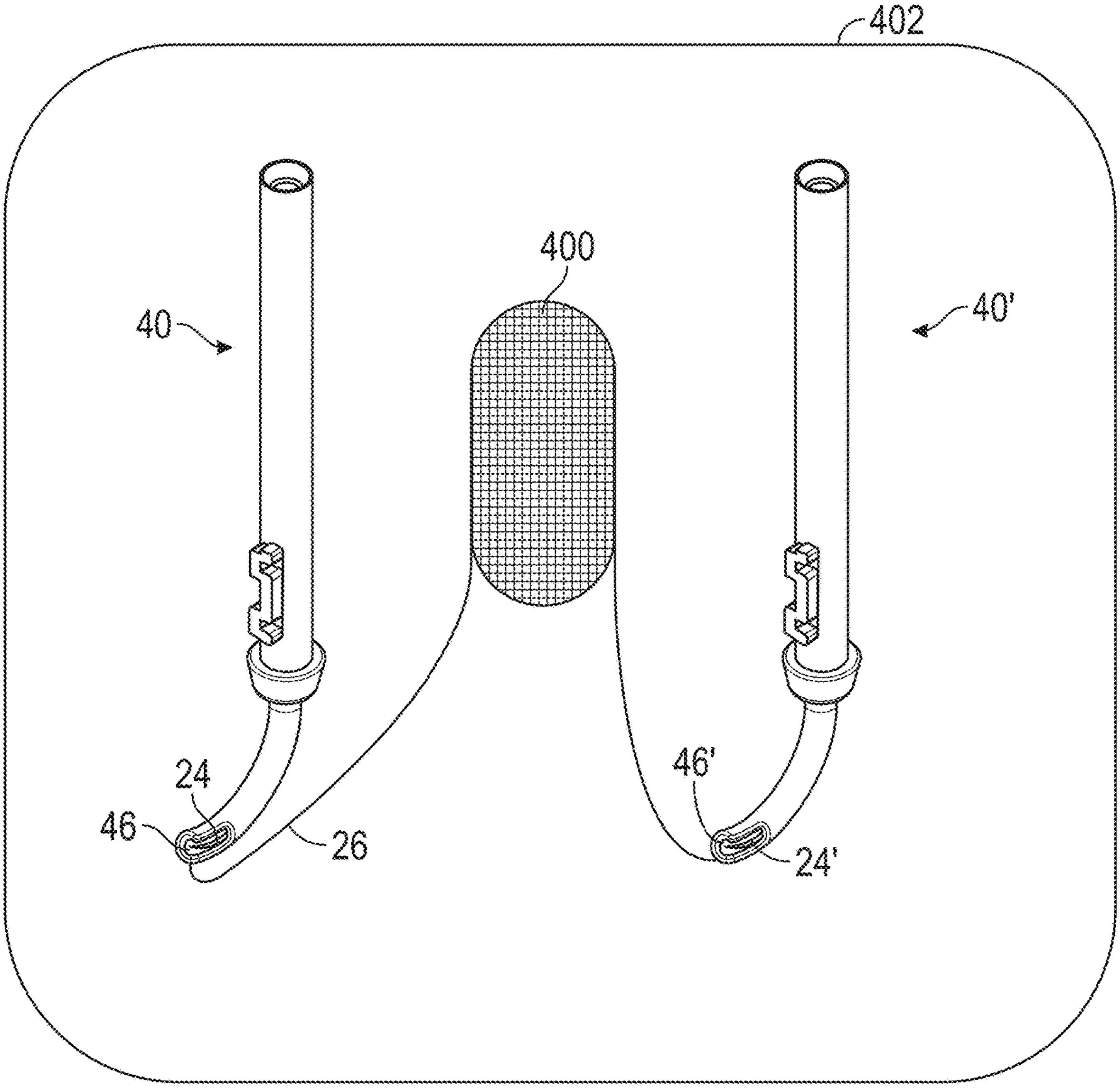
FIG. 11 is a schematic depiction of a kit including two distal end assemblies.

FIG. 11 depicts a kit including two distal end assemblies: a distal end assembly 40, which is also shown in FIGS. 2 and 6, and a second distal end assembly 40', which can be identical to the first distal end assembly 40. The suture 26 is connected with a connection end, e.g., the second end 110 in FIG. 2, of the needle 24, hereinafter the first needle, in the first distal end assembly 40 and a connection end, e.g., similar to the second end 110 in FIG. 2, of a second needle 24' in the second distal end assembly 40'. The suture 26 extends through the first distal opening 46 when the first needle 24 is received in the first needle compartment (see the needle compartment 42 in FIG. 2) prior to the first needle 24 being ejected from the first distal opening 46. The suture 26 also extends through the second distal opening 46' when the second needle 24' is received in the second needle compartment (similar to the needle compartment 42 in FIG. 2) prior to the second needle 24' being ejected from the second distal opening 46'. The suture 26 can be wrapped around a suture holder 400, and the suture holder 400 along with the two distal end assemblies 40, 40' can be provided in a package 402.

In use, two suturing devices, each similar to the suturing device 10 shown in FIG. 1, can be provided in a package similar to, for example, the package shown FIG. 7 in U.S. application Ser. No. 18/150,868. The suture 26 depicted in FIG. 2 is a double-armed suture having one needle 24 (see FIG. 2) disposed in one suturing device 10 and another similar needle (similar to FIG. 9) at the other end disposed in the other suturing device. One suturing device 10 is used to pass the needle 24 through tissue T on one side of a tear or incision, and the other suturing device is used to pass the other the other needle, which is connected with the suture 26, through tissue T on the other side of the tear or incision.

After ejecting the needles 24, each suturing device 10 will have the primer 114 in the depressed position shown in FIG. 4. The release buttons 200, which are aligned with the barbs 144, can then be depressed, which moves the barbs 144 away from the shoulder 146 and allows the primer 114 to be pulled towards the extended position, which is shown in FIG. 3. After the primer 114 has been pulled from the depressed position toward the extended position, the needle pusher 14 moves out of the needle passage 44, which is curved, and allows for rotation of the distal end assembly 40, 40*a*, 40*b* with respect to the cannula 12, 12*a*, 12*b*, 12*c*. When the protrusion 72, 272, 372 aligns with the first arm 212, 242, 282, 382 in the slot 76, 236, 276, 376, the distal end assembly 40, 40*a*, 40*b* can be pulled out of and removed from the cannula 12, 12*a*, 12*b*, 12*c*. A replacement distal end assembly, such as the distal end assemblies 40, 40' shown in FIG. 11 can then be inserted into the suturing devices to continue with the suturing procedure.

A suturing device and kit have been described above with particularity. Modifications and alterations will occur to those upon reading and understanding the above detailed description. The invention, however, is not limited to only the embodiments described above. Instead, the invention is broadly defined by the appended claims and the equivalents thereof. It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A suturing device comprising:

a cannula;

a distal end assembly removably connected to the cannula, wherein the distal end assembly includes a needle compartment defining a needle passage terminating in a distal opening;

a needle pusher provided in the cannula and extending into the distal end assembly when the distal end assembly is connected with the cannula;

a primer movable between an extended position and a depressed position; and a spring positioned between the primer and the needle pusher, wherein movement of the primer from the extended position toward the depressed position compresses the spring to exert a biasing force on the needle pusher in an advance direction when the primer is in the depressed position, wherein the primer is operatively connected with the needle pusher such that movement of the primer from the depressed position toward the extended position moves the needle pusher in a retract direction, which is opposite the advance direction, wherein the distal end assembly includes an insert configured for being inserted into the cannula such that the needle pusher extends into the distal end assembly from the cannula when the distal end assembly is connected with the cannula, and wherein the insert includes a proximal end disposed in the cannula and a proximal angled surface inclined from an inner surface of the cannula toward an interior of the insert, wherein the proximal angled surface guides the needle pusher into the insert when the distal end assembly is being connected with the cannula.

2. The suturing device of claim 1, wherein the insert includes an outer surface that mates with an inner surface of the cannula in a sliding, snug fit relationship.

3. A suturing device comprising:

a cannula;

a distal end assembly removably connected to the cannula, wherein the distal end assembly includes a needle compartment defining a needle passage terminating in a distal opening;

a needle pusher provided in the cannula and extending into the distal end assembly when the distal end assembly is connected with the cannula;

a primer movable between an extended position and a depressed position; and a spring positioned between the primer and the needle pusher, wherein movement of the primer from the extended position toward the depressed position compresses the spring to exert a biasing force on the needle pusher in an advance direction when the primer is in the depressed position, wherein the primer is operatively connected with the needle pusher such that movement of the primer from the depressed position toward the extended position moves the needle pusher in a retract direction, which is opposite the advance direction, wherein the distal end assembly includes an insert configured for being inserted into the cannula such that the needle pusher extends into the distal end assembly from the cannula when the distal end assembly is connected with the cannula, and wherein one of the cannula and the insert defines a slot, and the other of the cannula and the insert includes a protrusion receivable in the slot for locking the cannula with the insert.

4. The suturing device of claim 3, wherein the slot includes a first arm extending in a direction in which the insert is inserted in the cannula, and the slot includes a second arm extending from the first arm in a direction perpendicular to the first arm, the second arm being configured to receive the protrusion to lock the insert with the cannula.

5. The suturing device of claim 4, wherein the insert includes a shoulder that abuts the cannula when the insert is inserted into the cannula a distance that positions the protrusion at a junction between the first arm and the second arm.

6. The suturing device of claim 4, wherein the protrusion is provided on the insert and the protrusion includes an elastic finger and a tab extended from the elastic finger, in the second arm a notch extends from the second arm parallel to the direction in which the insert is inserted in the cannula, and the elastic finger deforms inward against the cannula when the protrusion moves from the first arm into the second arm and expands outward when the tab aligns with the notch.

7. The suturing device of claim 4, wherein the protrusion is provided on the insert and the cannula includes a prong extending into the slot, in the second arm a notch extends from the second arm parallel to the direction in which the insert is inserted in the cannula, and the prong biases the protrusion toward the notch when the protrusion is received in the second arm of the notch.

8. A suturing device comprising:

a cannula;

a distal end assembly removably connected to the cannula, wherein the distal end assembly includes a needle compartment defining a needle passage terminating in a distal opening;

a needle pusher provided in the cannula and extending into the distal end assembly when the distal end assembly is connected with the cannula;

a primer movable between an extended position and a depressed position; and a spring positioned between the primer and the needle pusher, wherein movement of the primer from the extended position toward the depressed position compresses the spring to exert a biasing force on the needle pusher in an advance direction when the primer is in the depressed position, wherein the primer is operatively connected with the needle pusher such that movement of the primer from the depressed position toward the extended position moves the needle pusher in a retract direction, which is opposite the advance direction, wherein the distal end assembly includes an insert configured for being inserted into the cannula such that the needle pusher extends into the distal end assembly from the cannula when the distal end assembly is connected with the cannula, and wherein the distal end assembly includes a tube connected with the insert, the tube including a proximal section disposed in and at least partially surrounded by the insert and a distal section that forms the needle compartment defining the needle passage terminating in the distal opening, wherein the distal section extends from the proximal section and the insert.

9. The suturing device of claim 8, wherein the needle passage formed in the distal section is curved, and the distal end assembly further comprising:

a needle with a first end, which is pointed, and a second end opposite the first end, the needle being disposed in the needle passage; and a suture connected with the second end of the needle, wherein at least a portion of the suture extends through the distal opening when the needle is received in the needle compartment prior to the needle being ejected from the distal opening.

10. The suturing device of claim 8, wherein the proximal section of the tube includes a proximal chamfered surface inclined from an internal surface of the insert toward an interior of the tube, wherein the proximal chamfered surface guides the needle pusher into the tube when the distal end assembly is being connected with the cannula.

11. The suturing device of claim 10, wherein the insert includes a proximal end disposed in the cannula and a proximal angled surface inclined from an inner surface of the cannula toward an interior of the insert, wherein the proximal angled surface guides the needle pusher into the insert when the distal end assembly is being connected with the cannula, and the proximal angled surface being substantially aligned with the proximal chamfered surface to form a continuous inclined surface that guides the needle pusher into the insert and the tube when the distal end assembly is being connected with the cannula.

12. A distal end assembly for connecting with a cannula of an associated suturing device, the distal end assembly comprising:

an insert connectable with the cannula of the associated suturing device;

a tube connected with the insert, the tube including a proximal section disposed in and at least partially surrounded by the insert and a distal section that forms a needle compartment defining a needle passage terminating in a distal opening, wherein the distal section extends from the proximal section and the insert;

a needle with a first end, which is pointed, and a second end opposite the first end, the needle being disposed in the needle passage; and a suture connected with the second end of the needle, wherein the insert comprises:

a cylindrical outer surface to allow for rotation of the insert within the cannula; and at least one of a protrusion and a slot;

for the insert comprising the protrusion, the protrusion extends from the cylindrical outer surface and is configured to cooperate with the slot in the cannula when the insert is inserted into the cannula and rotated with respect to the cannula, and for the insert comprising the slot, the slot includes a first arm extending in a direction in which the insert is inserted in the cannula and a second arm extending from the first arm in a direction perpendicular to the first arm.

13. The distal end assembly of claim 12 for the insert comprising the protrusion, wherein the protrusion includes an elastic finger and a tab extended from the elastic finger.

14. The distal end assembly of claim 12, wherein the insert comprises a shoulder that extends from the cylindrical outer surface and abuts the cannula when the insert is connected with the cannula.

15. A distal end assembly for connecting with a cannula of an associated suturing device, the distal end assembly comprising:

an insert connectable with the cannula of the associated suturing device;

a tube connected with the insert, the tube including a proximal section disposed in and at least partially surrounded by the insert and a distal section that forms a needle compartment defining a needle passage terminating in a distal opening, wherein the distal section extends from the proximal section and the insert;

a needle with a first end, which is pointed, and a second end opposite the first end, the needle being disposed in the needle passage; and a suture connected with the second end of the needle, wherein the proximal section of the tube includes a proximal chamfered surface inclined from an internal surface of the insert toward an interior of the tube, wherein the proximal chamfered surface guides a needle pusher in the associated suturing device into the tube when the distal end assembly is being connected with the cannula.

16. The distal end assembly of claim 15, wherein the insert includes a proximal end configured to be disposed in the cannula and a proximal angled surface inclined from an outer surface of the insert toward an interior of the insert, wherein the proximal angled surface guides the needle pusher into the insert when the distal end assembly is being connected with the cannula.

17. The distal end assembly of claim 16, wherein the proximal angled surface is substantially aligned with the proximal chamfered surface to form a continuous inclined surface that guides the needle pusher into the insert and the tube when the distal end assembly is being connected with the cannula.

18. The distal end assembly of claim 15, wherein at least a portion of the suture extends through the distal opening when the needle is received in the needle compartment prior to the needle being ejected from the distal opening.

* * * * *